United States Patent [19]

De Francesco

[11] Patent Number: 5,336,212

[45] Date of Patent: Aug. 9, 1994

[54] ANTISEPTIC AND ANTIFERMENTATIVE SANITARY TOWELS PARTICULARLY NAPPIES AND PANTS, FOR INFANTS, WOMEN AND INCONTINENT ADULTS

[76] Inventor: Giovanni De Francesco, Via Carmelitani Pal.B6 Trappete, 95037 S. Giovanni La Punta (Catania), Italy

[21] Appl. No: 768,886

[22] PCT Filed: Dec. 27, 1989

[86] PCT No.: PCT/IT89/00084

§ 371 Date: Oct. 18, 1991

§ 102(e) Date: Oct. 18, 1991

[87] PCT Pub. No.: WO90/12555

PCT Pub. Date: Nov. 1, 1990

[30] Foreign Application Priority Data

Apr. 27, 1989 [IT] Italy .......................... 8904 B/89[U]

[51] Int. Cl.⁵ ............................................. A61F 13/15
[52] U.S. Cl. ..................................................... 604/360
[58] Field of Search ................ 604/358, 360; 424/430, 424/431, 445

[56] References Cited

U.S. PATENT DOCUMENTS

| | | | |
|---|---|---|---|
| 4,731,063 | 3/1988 | Newkirk | 604/360 |
| 5,045,322 | 9/1991 | Blank et al. | 604/360 |
| 5,103,500 | 4/1992 | Nages et al. | 604/359 |

*Primary Examiner*—Randall L. Green
*Assistant Examiner*—Rob Clarke
*Attorney, Agent, or Firm*—Michael J. Striker

[57] ABSTRACT

Sanitary towels in particular nappies, pants for infants, women, incontinent adults, treated with paraoxybenzoate of ethylene glycol phenyl undecyl ether, with chemical products in general having a bactericidal, fungicidal, antiseptic and antifermentative action.

11 Claims, No Drawings

ANTISEPTIC AND ANTIFERMENTATIVE SANITARY TOWELS PARTICULARLY NAPPIES AND PANTS, FOR INFANTS, WOMEN AND INCONTINENT ADULTS

The invention relates to sanitary towels in the form of nappies, pants and the like to he applied to the procto-uro-genital areas, for infants, women and incontinent adults.

Sanitary towels by their very nature collect and conserve organic liquids. These liquids, being excretions from the body, tend to decompose, generate unpleasant smells, infect and irritate the delicate and sensitive parts to which sanitary towels are applied.

The U.S. Pat. No. 3,093,546 discloses a means for effectively eliminating from sanitary towels the odour caused by the menstrual cycle.

Sanitary towels comprise a central specifically absorbent part surrounded by a permeable and filtering wrapping. According to the U.S. patent that part of the wrapping that comes in contact with the menstrual liquid (first claim) is impregnated with a deodorant made from water-insoluble halogenated diphenyl methane having the following structure:

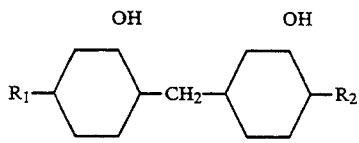

wherein $R_1$ and $R_2$ are hydrogen or chlorine. The compounds of this type include the chlorinated dihydroxy diphenyl methanes. This product is dissolved in a polyhydric alcohol possessing humectant properties and is confined to that part of the wrapping of the sanitary towel, that comes in contact with the menstrual liquid, by means of a water-soluble resin binder.

Due to the humectant properties of the hydric alcohol, the deodorant is found to be present on the surface of the water-soluble resin binder.

The deodorizing properties therefore become effective when the product comes in contact with the menstrual liquid. It is clear from the foregoing that the U.S. patent is characterized by a product confined to that part of the wraping of the sanitary towel that comes against the menstrual liquid.

This product dissolves when in contact with said menstrual liquid in which it exercises its deodorizing action. As the action of this chemical product is purely deodorant and specific to menstrual liquid, being further limited to the part of the towel encountering said liquid, the rest of the towel is left defenceless and without any antifermentative and fungicidal action.

It is actually a characteristic of the U.S. patent that the deodorant functions only when the chemical product comes in contact with the menstrual liquid and becomes a part of it without spreading to other parts of the towel. All the foregoing greatly limits the US invention both as regards its field of application (women's sanitary towels) and as regards the effect.

Subject of the invention, for which a patent is now applied, is the sanitary towel generally in its various forms of nappies, happy-pants and others, for use not only by women but also by children and incontinent adults. Such absorbing articles are impregnated with chemical preparations not only bacteriostatic and bactericidal but also fungicidal, antifermentative and generally antiseptic.

The entire towel is impregnated and therefore not only the internal fluffy part, but also the permeable and filtering wrapping enclosing it.

The treatment can be applied with advantage to the materials composing the fluff and its filtering wrapping. The chemical product used is a mixed solution of paraoxybenzoate of ethylene glycol phenyl undecyl ether, cetyltrimethylammonium chloride and distilled water.

Preferably the percentages are as follows:

Paraoxybenzoate of ethylene-glycol-phenyl-undecyl ether 25%

Cetyl-trimethyl-ammonium chloride, 28% solution 5%

Distilled water. 70%

The effects of the above preparation have been checked by numerous experiments.

The following are the results obtained at the "Institute of Health and Preventive Medicine" of the University of Catania on Sep. 1, 1989. 12 commercially available sanitary towels and 12 sanitary towels treated with the aforementioned chemical preparation were used.

The sanitary towels were impregnated by means of a spraying technique. A quantity equivalent to circa 1 ml of the product was distributed evenly on each sanitary towel. In order to test antibacterial activity at the outer surface of the sanitary towel, about 4 cm² of the surface layer of each sample were soaked with bacterial suspensions of two micro-organisms:

Gram-positive (*Staphylococcus aureus* ATCC 9144)
Gram-negative (*Escherichia coli* ATCC 25922).

The concentration of these suspensions was circa $10^5$ bacteria per ml.

After an hour of contact in an incubator set at 37° C., the samples were pressed onto the surface of a suitable culture medium (Mueller-Hinton's agar) contained in petri dishes. The dishes were then incubated at 37° C. for 24 hours. The number of colonies which had developed was then counted. The four columns of the table below give the results obtained:

column A gives the number of colony forming units (CFU) of *S. aureus* in 12 untreated sanitary towels;
column B gives the number of colony forming units (CFU) of *S. aureus* in 12 treated sanitary towels;
column C gives the number of colony forming units (CFU) of *E. coli* in 12 untreated sanitary towels;
column D gives the number of colony forming units (CFU) of *E. coli* in 12 treated sanitary towels.

TABLE

Number of colony forming units (CFU) of *S. aureus* and of *E. coli*

| | A | B | C | D |
|---|---|---|---|---|
| | 230 | 82 | 250 | 27 |
| | 202 | 80 | 230 | 5 |
| | 199 | 80 | 195 | 6 |
| | 366 | 150 | 190 | 7 |
| | 380 | 43 | 340 | 23 |
| | 215 | 90 | 180 | 0 |
| | 255 | 65 | 205 | 15 |
| | 389 | 71 | 132 | 9 |
| | 108 | 68 | 198 | 11 |
| | 263 | 102 | 150 | 7 |
| | 157 | 88 | 165 | 40 |
| | 336 | 114 | 218 | 21 |
| Average | 258 | 86 | 204 | 14 |
| Reduction in percentage | | 77% | | 93% |

As can be seen from this table, the averages of the units (CFU) of S. aureus were 258 for the untreated sanitary towels and 86 for those treated, while the averages of the units (CFU) of E. coli were 204 for the untreated sanitary towels and 14 for those treated.

Therefore the reduction in percentage obtained with the chemical preparation tested on the samples compared was 77% for the units (CFU) of S. aureus and 93% for the units (CFU) of E. coli.

Here follow the results obtained at the Health Department of Pavia University.

MATERIALS USED

A) Bands of cotton wool

Sanitary towels for women and nappy-pants for children
untreated, to serve as controls,
treated with the disinfectant referred to above.

B) Culture mediums used:

Müller-Hinton, for testing bacteriostatic activity
Leethen, for testing bactericidal activity.
Compositions of the two cultures:

| a) | Müller-Hinton: | | |
|---|---|---|---|
| | an infusion of meat | g | 6.0 |
| | hydrolyzed casein | g | 17.5 |
| | starch | g | 1.5 |
| | agar | g | 10.0 |
| | water | ml | 1000 |
| b) | Leethen: | | |
| | extract of ox meat | g | 3.0 |
| | tryptone | g | 5.0 |
| | dextrose | g | 1.0 |
| | agar | g | 15.0 |
| | sorbitan mono-oleate | g | 7.0 |
| | lecithin | g | 1.0 |
| | water | ml | 1000 |

C) Sterile equine serum

D) Tested micro-organisms

Experiments were made on the following species of bacteria:
Staphylococcus pyogenes aureus ATCC 61685
Escherichia coli ISM 6595
Candida albicans Coll. Zoop. Sper. BS 1250

METHOD FOLLOWED

Since the disinfectant mixture contains a compound of the quaternary ammonium group, whose bacteriostatic activity is described in literature on the subject as being high, the experiments were planned so as to differentiate the mixture's activity between bacteriostatic and bactericidal.

A feature common to disinfectants of the quaternary ammonium group is that of possessing high residual disinfecting power which remains intact over a period of time and becomes active when the disinfecting substance dissolves in the fluids contained in organic products. The experiments were therefore planned and carried out under differing experimental conditions, namely, following the usual laboratory method for testing the anti-microbic power of disinfectants generally (use of microbic suspensions in physiological solutions) and using microbic suspensions in physiological solutions, to which 20% of sterile equine serum has been added, to show up any possible interference by organic material on the disinfecting effect obtained.

The method employed for studying antimicrobic activity consisted in cutting out a circular piece, diameter 6.5 cm, equivalent to an area of 33.16 $cm^2$, of the two layers that form the inner surface of the sanitary towel for women, and another piece of the same size constituting the inner surface of the nappy-pants.

Each of these discs was immersed for 5 seconds in a suitably diluted suspension of each of the above-named microorganisms, and then laid on a sterile plate where it was left for 1 hour or for 3 hours according to the experiment in progress.

At the expiry of that time the disc was carefully placed to adhere to the surface of the culture prepared either for the bacteriostatic test or for the bactericidal test. Three minutes after that, the disc was removed and the dish put into an incubator at 37° C. for 24 hours in the cases of staphylococcus aureus and escherichia coli and for 48 hours for candida albicans.

The colonies found to be developed were then counted. Together with the direct test on activity described above, a study was also made, already referred to, on the possible interference by organic material on the disinfecting mixture's antibacterial effect.

To do this the bacterial suspension, in which the disc to be tested was placed, was prepared with the addition of 20% of sterile equine serum.

Results of tests on anti-microbic activity by bands of cotton-wool (sanitary towels for women and nappy-pants for children, treated with disinfectant. (The FIGURES in columns headed 'treated' and 'control' are per unit and represent average values obtained from the results of 30 tests made.)

| | SANITARY TOWELS FOR WOMEN | | | NAPPY-PANTS FOR CHILDREN | | |
|---|---|---|---|---|---|---|
| | treated | control | % reduction | treated | control | % reduction |
| *Staphylococcus pyogenes aureus* | | | | | | |
| 1. without serum: after contact for 1 hour | | | | | | |
| bacteriostatic activity | 1 | 341 | 99.7 | 0 | 310 | 100.0 |
| bactericidal activity | 1 | 308 | 99.6 | 0 | 290 | 100.0 |
| 2. with 20% serum added | | | | | | |
| a) after contact for 1 hour | | | | | | |
| bacteriostatic activity | 1 | 295 | 99.6 | 0 | 146 | 100.0 |
| bactericidal activity | 23 | 230 | 90.0 | 3 | 114 | 97.4 |
| b) after contact for 3 hours | | | | | | |
| bacteriostatic activity | 1 | 360 | 99.7 | 0 | 132 | 100.0 |
| bactericidal activity | 23 | 360 | 93.4 | 0 | 126 | 100.0 |
| *Escherichia coli* | | | | | | |
| 1. without serum: after contact for 1 hour | | | | | | |
| bacteriostatic activity | 18 | 142 | 87.4 | 9 | 306 | 97.1 |

-continued

Results of tests on anti-microbic activity by bands of cotton-wool (sanitary towels for women and nappy-pants for children, treated with disinfectant. (The FIGURES in columns headed 'treated' and 'control' are per unit and represent average values obtained from the results of 30 tests made.)

| | SANITARY TOWELS FOR WOMEN | | | NAPPY-PANTS FOR CHILDREN | | |
|---|---|---|---|---|---|---|
| | treated | control | % reduction | treated | control | % reduction |
| bactericidal activity | 17 | 126 | 86.5 | 9 | 207 | 95.7 |
| 2. with 20% serum added | | | | | | |
|   a) after contact for 1 hour | | | | | | |
|     bacteriostatic activity | 48 | 150 | 68.0 | 7 | 164 | 95.7 |
|     bactericidal activity | 58 | 134 | 56.8 | 23 | 114 | 79.8 |
|   b) after contact for 3 hours | | | | | | |
|     bacteriostatic activity | 9 | 182 | 95.0 | 6 | 163 | 96.4 |
|     bactericidal activity | 5 | 158 | 96.8 | 2 | 164 | 98.8 |
| *Candida albicans* | | | | | | |
| without serum: after contact for 1 hour | | | | | | |
|   bacteriostatic activity | 1 | 312 | 99.7 | 0 | 205 | 100.0 |
|   bactericidal activity | 2 | 142 | 98.6 | 1 | 309 | 99.7 |

RESULTS

The results of the tests made, given in the preceding table, are expressed as averages (arithmetical average) of the 30 repetitions executed, from which the percentage reductions of micro-oraganisms, exterminated by the disinfectant's bacteriostatic and bactericidal activity, were calculated.

A study of the table shows:

the high level of antibacterial (bacteriostatic and bactericidal) activity of the two bands of cotton-wool (sanitary towels for women and nappy-pants for small children) against both *staphylococcus aureus* and *candida albicans;* activity of a less marked degree in relation to *escherichia coli*, especially as concerns the sanitary towels.

The advantages of the invention are clear.

Using simple means which do not involve complex and costly systems, virtually all the negative consequences arising from the accumulation of harmful and decomposing substances and, due to the actual nature of sanitary towels, contact between such substances and delicate parts of the human body, are both prevented and fought, avoiding above all irritation, infection and unpleasant smells.

In particular, disinfectant action is extended over the whole sanitary towel and this is done irrespective of the menstrual cycle.

As the tests made by the Health Department of Pavia University clearly bring out, there is also considerable opposition to *Candida albicans*, a parassitic fungus causing disease in man commonly found on mucous surfaces, and this activity is of special importance in the case of sanitary towels.

I claim:

1. Sanitary towels, for organic liquids issuing from the procto-uro-genital areas of the human body, in the form of plugs, panties and the like for women, children, incontinent adults, comprising: impregnation with a chemical preparation possessing high residual disinfecting action that remains unaltered over a period of time and that is activated by reaction with the body liquids thus eliminating or combatting, at the outset, proliferation of bacteria, fungi, fermentation, irritation and unpleasant smells, the chemical preparation being composed of paraoxybenzoate of ethylene-glycol-phenyl-undecyl-ether.

2. Sanitary towels as defined in claim 1, in which the chemical preparation is activated by human body liquids through solubilization.

3. Sanitary towels as defined in claim 1, in which impregnation by the chemical preparation occurs in all the materials making up the sanitary towel.

4. Sanitary towels as defined in claim 1, in which the fluff is impregnated with the chemical preparation.

5. Sanitary towels as defined in claim 1, in which both the fluff and the filtering covers over it are impregnated with the chemical preparation.

6. Sanitary towels, for organic liquids issuing from the procto-uro-genital areas of the human body, in the form of plugs, panties and the like for women, children, incontinent adults, comprising: impregnation with a chemical preparation possessing high residual disinfecting action that remains unaltered over a period of time and that is activated by reaction with the body liquids thus eliminating or combatting, at the outset, proliferation of bacteria, fungi, fermentation, irritation and unpleasant smells, the chemical preparation composed of paraoxybenzoate of ethylene-glycol-phenyl-undecyl-ether being solubilized in distilled water with the aid of cetyl trimethyl ammonium chloride.

7. Sanitary towels as defined in claim 6, in which the chemical preparation is activated by human body liquids through solubilization.

8. Sanitary towels as defined in claim 6, in which impregnation by the chemical preparation occurs in all the materials making up the sanitary towel.

9. Sanitary towels, for organic liquids issuing from the procto-uro-genital areas of the human body, in the form of plugs, panties and the like for women, children, incontinent adults, comprising: impregnation with a chemical preparation possessing high residual disinfecting action that remains unaltered over a period of time and that is activated by reaction with the body liquids thus eliminating or combatting, at the outset, proliferation of bacteria, fungi, fermentation, irritation and unpleasant smells, the percentages of the components of the chemical preparation being:

paraoxybenzoate of ethylene-glycol-phenyl-undecyl-ether: 25%

Cetyl-trimethyl-ammonium chloride in a 28% solution: 5%

Distilled Water: 70%.

10. Sanitary towels as defined in claim 9, in which the chemical preparation is activated by human body liquids through solubilization.

11. Sanitary towels as defined in claim 9, in which impregnation by the chemical preparation occurs in all the materials making up the sanitary towel.

* * * * *